(12) United States Patent
Ivosev et al.

(10) Patent No.: US 7,865,322 B2
(45) Date of Patent: Jan. 4, 2011

(54) RELATIVE NOISE

(75) Inventors: Gordana Ivosev, Etobicoke (CA); Ronald Bonner, Newmarket (CA); Min Yang, Maple (CA)

(73) Assignee: DH Technologies Development Pte. Ltd., Singapore (SG)

( * ) Notice: Subject to any disclaimer, the term of this patent is extended or adjusted under 35 U.S.C. 154(b) by 400 days.

(21) Appl. No.: 12/102,537

(22) Filed: Apr. 14, 2008

(65) Prior Publication Data

US 2009/0259438 A1   Oct. 15, 2009

(51) Int. Cl.
*G06F 15/00* (2006.01)
*H04B 15/00* (2006.01)

(52) U.S. Cl. .................... 702/69; 702/189; 702/191

(58) Field of Classification Search .............. 702/69, 702/189, 191
See application file for complete search history.

(56) References Cited

U.S. PATENT DOCUMENTS

| | | |
|---|---|---|
| 4,628,529 A | 12/1986 | Borth et al. |
| 7,340,375 B1 | 3/2008 | Patenaud et al. |
| 2004/0215396 A1 * | 10/2004 | Christie et al. ............ 702/14 |
| 2006/0144126 A1 | 7/2006 | O'Brien et al. |
| 2008/0059072 A1 | 3/2008 | Willen et al. |

* cited by examiner

*Primary Examiner*—Bryan Bui
(74) *Attorney, Agent, or Firm*—John R. Kasha; Kasha Law LLC

(57) ABSTRACT

Relative noise is a single scalar value that is used to predict the maximum value of the expected noise at any point and is calculated from the measured signal and a mathematical noise model. The mathematical noise model is selected or estimated from an observation that includes statistical and/or numerical modeling based on a population of measurement points. An absolute noise for a plurality of points of the measured signal is estimated. An array of values is calculated by dividing each of a plurality of points of the absolute noise by a corresponding expected noise value calculated from the mathematical noise model. The relative noise is calculated by taking a standard deviation of a plurality of points of the array. The relative noise can be used to calculate scaled background signal noise, filter regions, denoise data, detect false positives from features, calculate S/N, and determine a stop condition for acquiring data.

38 Claims, 2 Drawing Sheets

RELATIVE NOISE

INTRODUCTION

Determining whether or not a given data point is significant is a common problem in data processing. A mass spectrometry data point, for example, is significant if it can be attributed to a real peak rather than the underlying background signal plus noise. Generally a data point that is large compared to the expected noise is significant. However, such a comparison is more difficult as the noise gets larger or the data point gets smaller. Such a comparison is also difficult in regions where there are few or no data points adjacent to the data point of interest. In these regions, there are too few data points to accurately model the expected noise.

DRAWINGS

The skilled person in the art will understand that the drawings, described below, are for illustration purposes only. The drawings are not intended to limit the scope of the applicant's teachings in any way.

Figure 1:
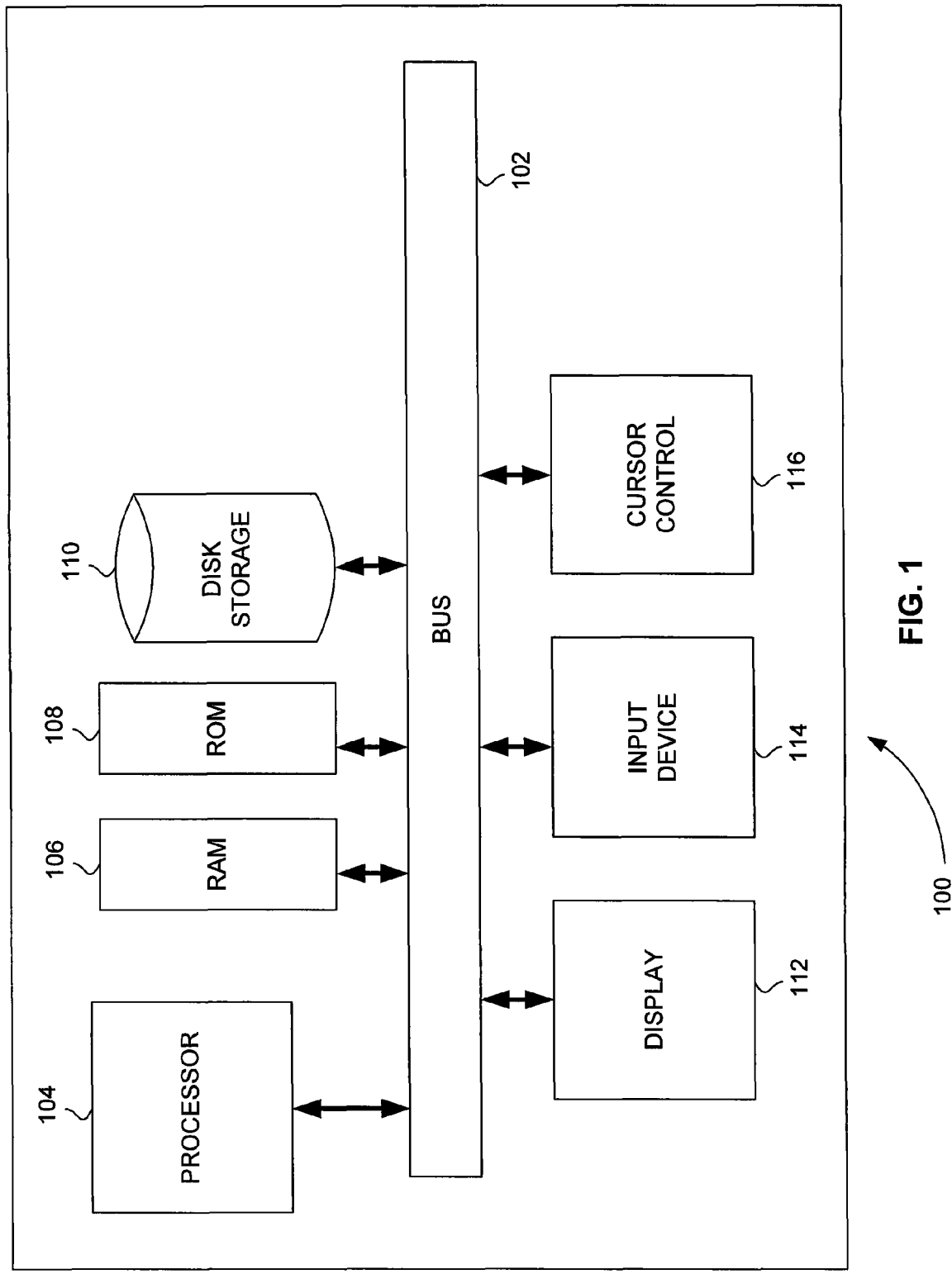
FIG. 1 is a block diagram that illustrates a computer system, upon which embodiments of the present teachings may be implemented.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF VARIOUS EMBODIMENTS

The section headings used herein are for organizational purposes only and are not to be construed as limiting the subject matter described in any way. Embodiments of systems and methods related to relative noise are described in this detailed description.

Computer Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for determining base calls, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium can include, but is not limited to, a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Methods of Data Processing

One method for determining the significance of a data point includes measuring the signal-to-noise ratio (S/N). Measuring the S/N works well when the measured signal is large compared to the measured or estimated noise. Measuring the S/N becomes more difficult as the noise gets larger or the measured signal gets smaller. Also, measuring the S/N to determine the significance of a data point becomes more difficult if the noise changes across the data or depends on the data in some way.

In various embodiments, a measured signal from a mass spectrometer, for example, can include an underlying signal and an absolute noise. The underlying signal, in turn, can include a background signal and the signal of interest. The underlying signal can be, for example, the signal produced by a sample. The background signal can be, for example, a signal component of the underlying signal that has no information that is characteristic of the sample. Such a background signal is, therefore, uninteresting from a biological or chemical point of view. In various embodiments, the background signal can be mostly ion source dependant and independent variable (mass to charge ratio (m/z) or time) dependant. The signal of interest can be, for example, one or more signal components of the underlying signal that carry significant information about the sample. The absolute noise of the measured signal, therefore, can include background noise from the background signal and noise from the signal of interest.

In various embodiments, the noise of a mass spectrometer can depend on the data. For example, if the mass spectrometer is modeled as a pulse counting system, the noise can be governed by Poisson statistics. As a result, the variance of the data is the same as its mean, so the standard deviation, and hence some part of the noise, is calculated from the square root of the mean of the data. In other words, the noise of a mass spectrometer can be estimated from a mathematical noise model that depends on the square root of the signal intensity. Using this mathematical noise model, it is possible to calculate the expected noise from one known point of interest (signal intensity) of the measured signal.

In various embodiments, a single scalar value can be used to predict the expected noise range at any point in the data. This expected noise can then be compared to a measured signal or an underlying signal to determine the significance of the signal. The single scalar value that can be used is called relative noise, for example.

Figure 2:
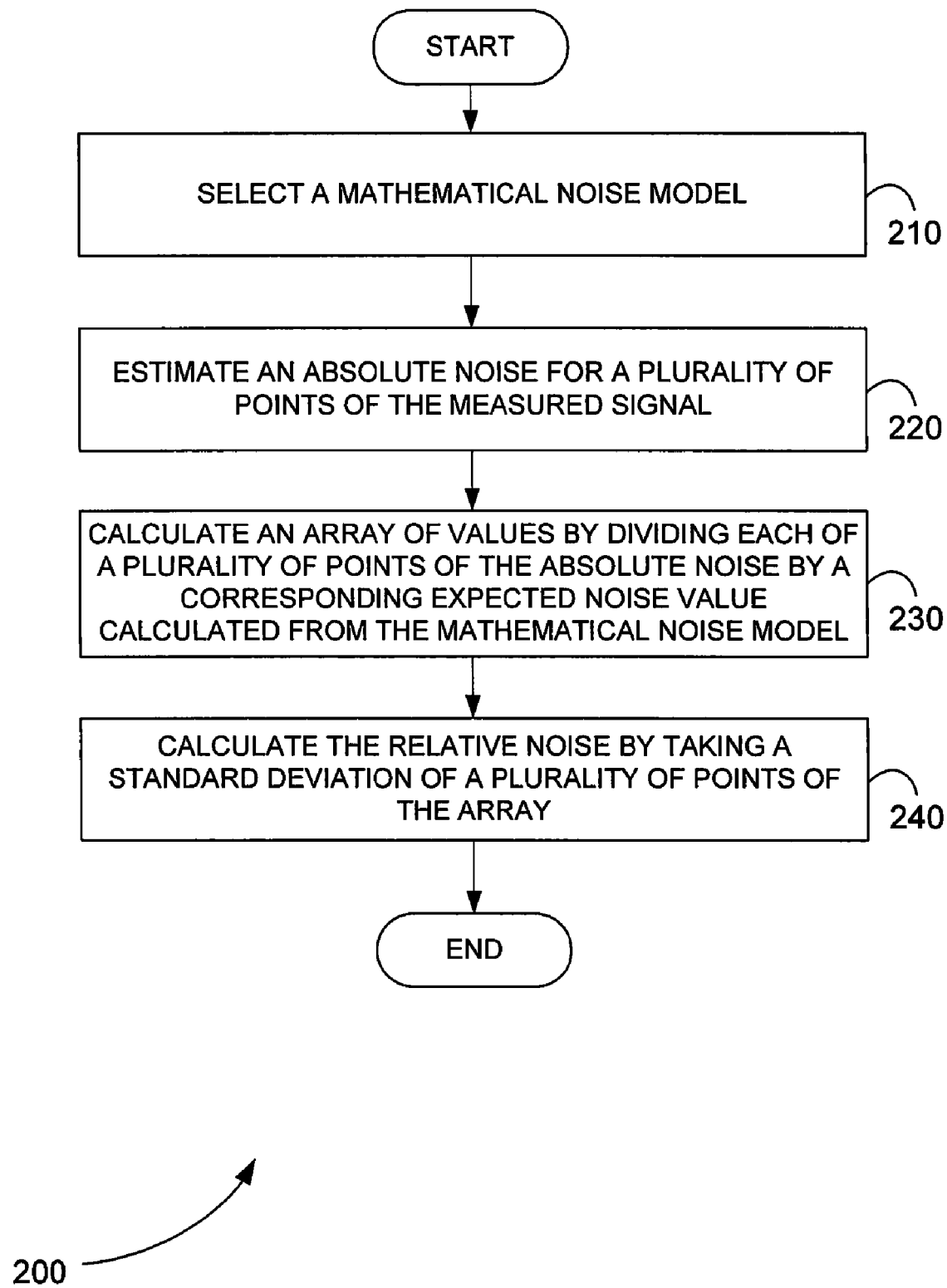
FIG. 2 is a flowchart showing a method for calculating the relative noise of a measured signal, in accordance with the present teachings.

FIG. 2 is a flowchart showing a method 200 for calculating the relative noise of a measured signal, in accordance with the present teachings.

In step 210 of method 200, a mathematical noise model is selected. The mathematical noise model can be selected, for example, based on knowledge about a data acquisition process of the measured signal. In various embodiments, the mathematical noise model can be selected based on an observation made from the measured signal. The observation can include, for example, statistical and/or numerical modeling based on a population of measurement points.

In step 220, an absolute noise for a plurality of points of the measured signal is estimated. The absolute noise can be estimated, for example, by subtracting an estimate of an underlying signal from the measured signal. An estimate of the underlying signal can be obtained, for example, by smoothing the measured signal. In various embodiments, an estimate of the underlying signal can be obtained by applying a noise filter to the measured signal.

In various embodiments, the absolute noise can be estimated by applying a filter to the measured signal. The underlying signal can then be estimated by subtracting the estimated absolute noise from the measured signal.

In step 230, an array of values is calculated by dividing each of a plurality of points of the absolute noise by a corresponding expected noise value calculated from the mathematical noise model.

In step 240, the relative noise is calculated by taking a standard deviation of a plurality of points of the array.

In various embodiments, a computer system is used to calculate the relative noise of a measured signal. The computer system can be, but is not limited to, computer system 100, shown in FIG. 1 and described above. The computer system includes a processor. The processor selects a mathematical noise model. The processor estimates an absolute noise for a plurality of points of the measured signal. The processor calculates an array of values by dividing each of a plurality of points of the absolute noise by a corresponding expected noise value calculated from the mathematical noise model. Finally, the processor calculates the relative noise by taking a standard deviation of a plurality of points of the array.

In various embodiments, the relative noise can be used to calculate a scaled noise. An expected noise is predicted using the mathematical noise model and a signal. The signal can be a one-dimensional signal or a two-dimensional signal, for example. The signal can be, but is not limited to, a background signal, an underlying signal, a signal of interest, or the measured signal. The background signal, underlying signal, and signal of interest can be estimated, for example. The scaled noise is calculated by multiplying the expected noise by the relative noise. The signal and the scaled noise can be used in a number of applications.

EXAMPLES

Aspects of the applicant's teachings may be further understood in light of the following examples, which should not be construed as limiting the scope of the present teachings in any way.

In various embodiments, the relative noise can be used to determine if a region of a signal includes a signal of interest. A region of a signal, for example, includes one or more neighboring sampling points of the signal. The signal can be the measured signal or the underlying signal, for example. As described above, the relative noise can be used to calculate a scaled background signal noise. The sum of the scaled background signal noise in the region and the estimated background signal in the region is compared with the signal in the region. If the signal in the region is greater than this sum, the region is determined to include a signal of interest.

In various embodiments, the relative noise can be used to determine if two features of a signal overlap and should be analyzed together. The two features of the signal are, for example, a first feature and a second feature. The first feature and the second feature are adjacent features, for example. A point of the signal that is between the first feature and the second feature is selected. The sum of a background signal value at the point and a scaled background signal noise value at the point is compared with the signal value at the point. If the signal value at the point is greater than the sum at the point, then the first feature and the second feature overlap and are analyzed together.

In various embodiments, a feature can include a group of neighboring data points in the signal. The signal can include one-dimensional and two-dimensional data. For example, the signal can include, but is not limited to, liquid chromatography mass spectrometry (LCMS) data, image data, a mass spectrum, or a chromatogram.

In various embodiments, the relative noise can be used to determine if a second feature of a signal is a real, separate feature and not part of first feature of the signal. A first feature signal is estimated using the first feature, the signal, and a mathematical model for a feature. An expected first feature noise is predicted using the mathematical noise model, the first feature signal and the background signal. A scaled first feature noise is calculated by multiplying the expected first feature noise by the relative noise. The sum of a background signal value at the second feature, a first feature signal value at the second feature, and a scaled first feature noise value at the second feature is compared with a signal value at the second feature. If the signal value is greater than the sum, the second feature is determined to be the real, separate feature. If the signal value is not greater than the sum, the second feature is a false positive, for example.

In various embodiments, the relative noise can be used to denoise a point of a signal. Denoising data involves decreasing data points likely to be noise, while leaving data points less likely to be noise unchanged. Those data points most likely to be noise are decreased the most. A scaled background signal noise value at a point of the signal is compared with the difference between the signal value at the point and a background signal value at the point. If the difference is smaller than the scaled background signal noise value, a value of zero is assigned to the point. If the difference exceeds the scaled background signal noise value by a value greater than zero but less than a threshold, the product of the difference and a multiplier is assigned to the point. The multiplier is, for example, a scalar value between zero and one. If the difference exceeds the scaled background signal noise value by a value greater than or equal to the threshold, the difference is assigned to the point.

In various embodiments, relative noise can be used to calculate the noise component for a calculation of the S/N. The S/N at a point of a signal is calculated by dividing the difference between a signal value at the point and a background signal value at the point by a product of the relative noise and a noise value at the point. The noise value can be, but is not limited to, a background signal noise value or an underlying signal noise value.

In various embodiments, the S/N at a point of the measured signal can be used to determine a stop condition for acquiring the measured signal. If the S/N is greater than or equal to a threshold S/N, acquisition of the measured signal is stopped.

In various embodiments, the relative noise of the measured signal can be used to determine a stop condition for acquiring the measured signal. If the relative noise is less than or equal to a threshold value, acquisition of the measured signal is stopped. The relative noise can get smaller and smaller as the length of data acquisition of the measured signal increases. In mass spectroscopy, longer data acquisition can imply that more spectra are averaged. If there is no signal of interest on top of the background signal, the measured signal or the underlying signal does not increase no matter how long data is acquired. However, the relative noise can continue to decrease, because the background signal can get smoother and smoother.

While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A method for calculating a relative noise of a measured signal, comprising:
    selecting a mathematical noise model;
    estimating an absolute noise for a plurality of points of the measured signal;
    calculating a plurality of expected noise values from the mathematical noise model for each of the plurality of points;
    calculating an array of values by dividing each of a plurality of points of the absolute noise by a corresponding expected noise value from the plurality of expected noise values; and
    calculating the relative noise by taking a standard deviation of a plurality of points of the array.

2. The method of claim 1, wherein the mathematical noise model is selected based on knowledge about a data acquisition process of the measured signal.

3. The method of claim 1, wherein the mathematical noise model is selected based on an observation made from the measured signal.

4. The method of claim 1, further comprising estimating an underlying signal from the measured signal.

5. The method of claim 4, wherein the absolute noise is estimated by subtracting the underlying signal from the measured signal.

6. The method of claim 4, wherein the underlying signal is obtained by smoothing the measured signal.

7. The method of claim 4, wherein the underlying signal is obtained by applying a noise filter to the measured signal.

8. The method of claim 1, wherein the absolute noise is estimated by applying a filter to the measured signal.

9. The method of claim 8, wherein an underlying signal is estimated by subtracting the absolute noise from the measured signal.

10. The method of claim 1, further comprising:
predicting an expected noise using the mathematical noise model and a signal; and
calculating a scaled noise by multiplying the expected noise by the relative noise.

11. The method of claim 10, wherein the signal comprises an underlying signal.

12. The method of claim 10, wherein the signal comprises a signal of interest.

13. The method of claim 10, wherein the signal comprises the measured signal.

14. The method of claim 1, further comprising:
estimating a background signal;
predicting an expected background signal noise using the mathematical noise model and the background signal; and
calculating a scaled background signal noise by multiplying the expected background signal noise by the relative noise.

15. The method of claim 14, further comprising determining if a region of a signal includes a signal of interest by:
comparing a sum of a background signal value of the background signal in the region and a scaled background signal noise value of the scaled background signal noise in the region with a signal value of the signal in the region; and
if the signal value is greater than the sum, determining that the region comprises the signal of interest.

16. The method of claim 15, wherein the signal comprises the measured signal.

17. The method of claim 15, wherein the signal comprises an underlying signal.

18. The method of claim 14, further comprising determining if a first feature of a signal and an adjacent second feature of the signal are analyzed together by:
selecting a point of the signal that is between the first feature and the second feature;
comparing a sum of a background signal value of the background signal at the point and a scaled background signal noise value of the scaled background signal noise at the point with a signal value of the signal at the point; and
if the signal value is greater than the sum, analyzing the first feature and the second feature together.

19. The method of claim 18, wherein the first feature comprises a first group of neighboring data points in the signal and the second feature comprises a second group of neighboring data points in the signal.

20. The method of claim 18, wherein the signal comprises liquid chromatography mass spectrometry data.

21. The method of claim 18, wherein the signal comprises image data.

22. The method of claim 18, wherein the signal comprises a mass spectrum.

23. The method of claim 18, wherein the signal comprises a chromatogram.

24. The method of claim 18, wherein the signal comprises the measured signal.

25. The method of claim 18, wherein the signal comprises an underlying signal.

26. The method of claim 14, further comprising determining if a second feature of a signal is a separate feature and not part of an adjacent first feature of the signal by:
estimating a first feature signal using the first feature, the signal, and a mathematical model for a feature;
predicting an expected first feature noise using the mathematical noise model, the first feature signal, and the background signal;
calculating a scaled first feature noise by multiplying the expected first feature noise by the relative noise;
comparing a sum of a background signal value of the background signal at the second feature, a first feature signal value of the first feature signal at the second feature, and a scaled first feature noise value of the scaled first feature noise at the second feature with a signal value of the signal at the second feature; and
if the signal value is greater than the sum, determining that the second feature comprises the separate feature.

27. The method of claim 26, wherein the signal comprises the measured signal.

28. The method of claim 26, wherein the signal comprises an underlying signal.

29. The method of claim 14, further comprising denoising a point of a signal by:
comparing a scaled background signal noise value of the scaled background signal noise at the point with a difference between a signal value of the signal at the point and a background signal value of the background signal at the point;
if the difference is smaller than the scaled background signal noise value, assigning a value of zero to the point;
if the difference exceeds the scaled background signal noise value by a value greater than zero but less than a threshold, assigning a product of the difference and a multiplier to the point; and
if the difference exceeds the scaled background signal noise value by a value greater than or equal to the threshold, assigning the difference to the point.

30. The method of claim 29, wherein the signal comprises the measured signal.

31. The method of claim 29, wherein the signal comprises an underlying signal.

32. The method of claim 14, further comprising calculating a signal-to-noise ratio at a point of a signal by:
dividing a difference between a signal value of the signal at the point and a background signal value of the background signal at the point by a product of the relative noise and a noise value at the point.

33. The method of claim 32, wherein the noise value comprises an underlying signal noise value.

34. The method of claim 32, wherein the noise value comprises a background signal noise value.

35. The method of claim 32, further comprising:
if the signal-to-noise ratio is greater than or equal to a threshold signal-to-noise ratio, stopping acquisition of the measured signal.

36. The method of claim 32, further comprising:
if the relative noise is less than or equal to a threshold signal-to-noise ratio, stopping acquisition of the measured signal.

37. A non-transitory computer-readable medium containing computer instructions stored therein, for calculating a relative noise of a measured signal, causing a computer processor to perform:
selecting a mathematical noise model;
estimating an absolute noise for a plurality of points of the measured signal;
calculating a plurality of expected noise values from the mathematical noise model for each of the plurality of points;

calculating an array of values by dividing each of a plurality of points of the absolute noise by a corresponding expected noise value from the plurality of expected noise values; and calculating the relative noise by taking a standard deviation of a plurality of points of the array.

38. A computing system for calculating a relative noise of a measured signal, comprising:

a computer processor programmed to calculate the relative noise of the measured signal that, when executed by the computer processor:

selects a mathematical noise model, estimates an absolute noise for a plurality of points of the measured signal, calculates a plurality of expected noise values from the mathematical noise model for each of the plurality of points, calculates an array of values by dividing each of a plurality of points of the absolute noise by a corresponding expected noise value from the plurality of expected noise values, and calculates the relative noise by taking a standard deviation of a plurality of points of the array.

* * * * *